(12) United States Patent
Windrix

(10) Patent No.: US 11,234,930 B2
(45) Date of Patent: Feb. 1, 2022

(54) EMULSIFIED OILS AND BLENDS

(71) Applicant: Jesse Windrix, Allen, TX (US)

(72) Inventor: Jesse Windrix, Allen, TX (US)

(*) Notice: Subject to any disclaimer, the term of this patent is extended or adjusted under 35 U.S.C. 154(b) by 0 days.

(21) Appl. No.: 16/847,027

(22) Filed: Apr. 13, 2020

(65) Prior Publication Data
US 2020/0237665 A1 Jul. 30, 2020

Related U.S. Application Data

(63) Continuation-in-part of application No. 16/157,705, filed on Oct. 11, 2018, now Pat. No. 10,617,128, which is a continuation-in-part of application No. 15/729,806, filed on Oct. 11, 2017, now Pat. No. 10,687,541.

(51) Int. Cl.
| | | |
|---|---|---|
| A61K 9/107 | (2006.01) |
| A61K 31/20 | (2006.01) |
| A61K 31/202 | (2006.01) |
| A61K 36/185 | (2006.01) |
| A61K 36/736 | (2006.01) |
| A61K 36/22 | (2006.01) |
| A61K 36/54 | (2006.01) |
| A61K 47/24 | (2006.01) |
| A61K 47/12 | (2006.01) |
| A61K 47/36 | (2006.01) |
| A61K 47/40 | (2006.01) |
| A61K 31/197 | (2006.01) |
| A61K 9/00 | (2006.01) |
| A23D 7/015 | (2006.01) |
| A23D 7/005 | (2006.01) |
| A23L 9/20 | (2016.01) |
| A23L 33/12 | (2016.01) |
| A61K 35/60 | (2006.01) |

(52) U.S. Cl.
CPC ............ *A61K 9/107* (2013.01); *A23D 7/0053* (2013.01); *A23D 7/015* (2013.01); *A23L 9/24* (2016.08); *A23L 33/12* (2016.08); *A61K 9/0095* (2013.01); *A61K 31/197* (2013.01); *A61K 31/20* (2013.01); *A61K 31/202* (2013.01); *A61K 35/60* (2013.01); *A61K 36/185* (2013.01); *A61K 36/22* (2013.01); *A61K 36/54* (2013.01); *A61K 36/736* (2013.01); *A61K 47/12* (2013.01); *A61K 47/24* (2013.01); *A61K 47/36* (2013.01); *A61K 47/40* (2013.01); *A23V 2002/00* (2013.01)

(58) Field of Classification Search
CPC ...... A61K 9/107; A61K 31/20; A61K 31/202; A61K 36/185; A61K 36/736; A61K 36/22; A61K 36/54; A61K 47/24; A61K 47/12; A61K 47/36; A61K 47/40; A61K 9/0095; A61K 35/60; A23D 7/015; A23D 7/0053; A23L 9/24; A23L 33/12; A23V 2002/00
See application file for complete search history.

(56) References Cited

U.S. PATENT DOCUMENTS

| | | |
|---|---|---|
| 5,472,706 A | 12/1995 | Friedman |
| 2004/0052907 A1 | 3/2004 | Maniak et al. |
| 2004/0076731 A1 | 4/2004 | Bourke |
| 2006/0088574 A1* | 4/2006 | Manning .............. A23L 33/12 424/439 |
| 2009/0208472 A1 | 8/2009 | Sakai et al. |
| 2010/0092617 A1 | 4/2010 | Whittle |
| 2010/0233221 A1 | 9/2010 | Folmer et al. |
| 2018/0206518 A1* | 7/2018 | Silver |

FOREIGN PATENT DOCUMENTS

WO 2017180954 A1 10/2017

OTHER PUBLICATIONS

Meter Food, Lowering water activity with humectants: a step by step guide, 2017 (Year: 2017).*
International Search Report and Written Opinion (dated Jan. 7, 2019).

* cited by examiner

*Primary Examiner* — Cephia D Toomer
(74) *Attorney, Agent, or Firm* — Klemchuk LLP

(57) ABSTRACT

Coconut oil, coconut oil blends that are high in MCTs such as LouAna® liquid coconut oil, pure MCT oils, Omega-3 oils, cannabidiol (CBD), hemp extract, tree nut oil, macadamia oil, almond oil, cashew oil, avocado oil, docosahexaenoic acid (DHA), fish oil, and/or conjugated linoleic acid (CLA) may be emulsified to create an emulsified oil or blend that may take the form of a creamy shot or a cream substitute. These oils and/or blends may be emulsified using an emulsifier that may be selected from the following: sunflower lecithin, sodium stearoyl lactylate (SSL), acacia gum, beta-cyclodextrin, and combinations of same. By emulsifying these oils/oil blends, a good tasting creamy shot or a cream substitute can be formed.

17 Claims, No Drawings

EMULSIFIED OILS AND BLENDS

CROSS-REFERENCE TO RELATED APPLICATIONS

This application is a continuation-in-part of U.S. application Ser. No. 16/157,705 filed Oct. 11, 2018, which is a continuation-in-part of U.S. application Ser. No. 15/729,806 filed Oct. 11, 2017 entitled "Emulsified Oils and Blends," all of which are incorporated by reference in their entirety.

FIELD OF THE DISCLOSURE

The present disclosure generally relates to emulsified oils and blends, and more particularly to emulsified oils and blends emulsified with sunflower lecithin, sodium stearoyl lactylate (SSL), acacia gum, beta-cyclodextrin, or combinations of the same.

BACKGROUND

Medium-chain triglycerides (MCTs) are triglycerides that are believed to help in the process of excess calorie burning, leading to weight loss. MCTs are also believed to promote fat oxidation and reduced food intake. MCTs can be rapidly absorbed by the body. Rich sources for beneficial MCTs include palm kernel oil and coconut oil. While MCTs have been used as solvents for flavors, oral medicines, and vitamins, oils containing high levels of MCTs are rather unpalatable. Currently available products are barely palatable due to their oil profiles and/or flavors, and they typically are emulsified using Gum Arabic.

SUMMARY

Embodiments of the present disclosure may provide an emulsified oil, the emulsified oil comprising water; an oil selected from the group comprising: coconut oil, a coconut oil blend high in MCTs, pure MCT oil, Omega-3 oil, cannabidiol (CBD), hemp extract, tree nut oil, macadamia oil, almond oil, cashew oil, avocado oil, docosahexaenoic acid (DHA), fish oil, and/or conjugated linoleic acid (CLA); and an emulsifier selected from the group consisting of: sunflower lecithin, sodium stearoyl lactylate (SSL), acacia gum, beta-cyclodextrin, a combination of sunflower lecithin and SSL, and a combination of any of the previously listed emulsifiers, wherein the emulsified oil may contain up to approximately 1-5% by volume of the emulsifier. The water and the oil may be emulsified at a ratio of approximately 15:85 with up to approximately 1-5% by volume of the emulsifier to form an emulsified cream shot. The water and the oil may be emulsified at a ratio of approximately 51:49 with up to approximately 1-5% by volume of the emulsifier to form an emulsified cream substitute. The water and the oil may be combined with the emulsifier in a high shear mixer. Sound waves, such as through use of a sonicator, may create an emulsion to combine the water and the oil. The emulsified oil also may include one or more flavorings and/or sweeteners. The emulsified oil may further include L-carnitine. The emulsified oil may be a cream shot comprising 1500 mg of L-Carnitine per 15 mL shot. The emulsified oil may further comprise a humectant selected from the group comprising: glycerine, honey, sugar, syrup, sorbitol, aloe vera, egg yolk, and/or egg white. The emulsified oil also may further comprise collagen.

Other embodiments of the present disclosure may provide an emulsified cream shot, the emulsified cream shot comprising: water; an oil selected from the group comprising: coconut oil, a coconut oil blend high in MCTs, pure MCT oil, Omega-3 oil, cannabidiol (CBD), hemp extract, tree nut oil, macadamia oil, almond oil, cashew oil, avocado oil, docosahexaenoic acid (DHA), fish oil, and/or conjugated linoleic acid (CLA); and an emulsifier selected from the group consisting of: sunflower lecithin, sodium stearoyl lactylate (SSL), acacia gum, beta-cyclodextrin, a combination of sunflower lecithin and SSL, and a combination of any of the previously listed emulsifiers, wherein water and the oil may be emulsified at a ratio of approximately 15:85 with up to approximately 1-5% by volume of the emulsifier. The water and the oil may be combined with the emulsifier in a high shear mixer. The emulsified cream shot also may include one or more flavorings and/or sweeteners. The emulsified cream shot may further include L-carnitine. The cream shot may comprise 1500 mg of L-Carnitine per 15 mL shot.

Further embodiments of the present disclosure may provide an emulsified cream substitute, the emulsified cream substitute comprising: water; an oil selected from the group comprising: coconut oil, a coconut oil blend high in MCTs, pure MCT oil, Omega-3 oil, cannabidiol (CBD), hemp extract, tree nut oil, macadamia oil, almond oil, cashew oil, avocado oil, docosahexaenoic acid (DHA), fish oil, and/or conjugated linoleic acid (CLA); and an emulsifier selected from the group consisting of: sunflower lecithin, sodium stearoyl lactylate (SSL), acacia gum, beta-cyclodextrin, a combination of sunflower lecithin and SSL, and a combination of any of the previously listed emulsifiers, wherein water and the oil may be emulsified at a ratio of approximately 51:49 with up to approximately 1-5% by volume of the emulsifier. The water and the oil may be combined with the emulsifier in a high shear mixer. The emulsified cream substitute may also include one or more flavorings. The emulsified cream substitute may further include L-carnitine.

Other technical features may be apparent to one skilled in the art from the following descriptions and claims.

DETAILED DESCRIPTION

Embodiments of the present disclosure may emulsify coconut oil, coconut oil blends that are high in MCTs such as LouAna® liquid coconut oil, pure MCT oils, Omega-3 oils, cannabidiol (CBD), hemp extract, tree nut oil, macadamia oil, almond oil, cashew oil, avocado oil, docosahexaenoic acid (DHA), fish oil, and/or conjugated linoleic acid (CLA) to create a creamy shot or a cream substitute. These oils and/or blends may be emulsified using an emulsifier that may be selected from the following: sunflower lecithin, sodium stearoyl lactylate (SSL), acacia gum, beta-cyclodextrin, a combination of sunflower lecithin and SSL, or a combination of any of the previously listed emulsifiers. By emulsifying these oils/oil blends, a good tasting creamy shot or a cream substitute can be formed.

Selection of an emulsifier is typically based on the hydrophilic-lipophilic balance (HLB). According to common HLB calculations, sunflower lecithin, SSL, or a combination of sunflower lecithin and SSL should not work well in combination with coconut oil, coconut oil blends that are high in MCTs, pure MCT oils, and Omega-3 oils. However, these emulsifiers have been tested and provide for desired emulsified oils according to embodiments of the present disclosure. Sunflower lecithin is formed from the gum byproduct of dehydrating a sunflower seed and separating it; it has become more favored for many seeking an alternative to soy. SSL is an FDA-approved food additive that may be used to improve the mix tolerance and volume of processed foods.

In an embodiment of the present disclosure, a cream shot may be formed by emulsifying water and oil at a ratio of approximately 15:85 with up to approximately 1-5% by volume of emulsifier. Water and oil may be combined with the emulsifier in a high shear mixer and homogenized according to embodiments of the present disclosure. Inclusion of water in this ratio may allow the oil to become a creamy emulsion that acts as a carrier for water-soluble flavorings and/or sweeteners as described below.

Flavoring and/or sweeteners also may be included in the cream shot in some embodiments of the present disclosure. This embodiment is referred to as a cream shot in that it is meant to be ingested in a single shot as opposed to dispersing into a larger volume of liquid. This may provide the most oil content in a palatable form. In this embodiment of the present disclosure, any flavoring and/or sweetener may be dispersed evenly within the emulsion, as flavorings and/or sweeteners are typically water-soluble. In addition, as they are water-soluble, and not oil, an improved mouthfeel may be achieved.

In another embodiment of the present disclosure, a cream substitute may be formed by emulsifying water and oil at a ratio of approximately 51:49 with up to approximately 1-5% by volume of emulsifier. Water and oil may be combined with the emulsifier in a high shear mixer and homogenized according to embodiments of the present disclosure. In embodiments of the present disclosure, flavoring(s) also may be included in the cream substitute. The cream substitute may be mixed into beverages, such as coffee, in embodiments of the present disclosure.

Emulsified oils formed according to embodiments of the present disclosure also may include compounds, such as L-Carnitine. L-Carnitine is an amino acid that aids in weight loss. As explained in more detail below, by including L-Carnitine, the emulsified oil may become an even more effective diet aid. In the cream shot embodiment, L-Carnitine may be added to the cream shot to provide a dosage of approximately 1500 mg of L-Carnitine per 15 mL shot. This may result in dispensation of approximately 7 grams of MCT. However, it should be appreciated that higher dosages of L-Carnitine, such as 3000 mg per 15 mL, may be provided without departing from the present disclosure.

Inclusion of L-Carnitine as part of emulsified oils according to embodiments of the present disclosure may improve processing of non-MCT fats in a human's diet and in the body when used as part of a low-carb diet. For example, a person on a low-carb diet may use an emulsified oil containing L-Carnitine to gain an energy boost without his/her body being thrown out of ketosis. More specifically, when a person is on a low-carb diet, his/her body will eventually reach a state of ketosis, meaning that the body does not have adequate carbohydrate (glucose) intake to be fueled. Carbohydrates break down into glucose, which is then converted to glycogen. Glycogen is used to restore energy to cells in the body. Thus, when glycogen in the body has been exhausted, fat becomes the new fuel for the body. Fat stores in the liver can be processed by the body to release ketones. Ketones may then be used by the cells to restore energy, generally in a more effective manner than carbohydrates. As the body breaks down fat stores to create ketones, different fatty chains (short, medium and long) are broken down. Long chains can only be processed by the body when there are adequate levels of L-Carnitine because the long chains attach to L-Carnitine to be processed by the body and turned into energy. Accordingly, supplementing the emulsified oil according to embodiments of the present disclosure with L-Carnitine may provide greater fat loss potential during a ketosis-type diet. It should be appreciated that there may be some embodiments of the present disclosure where L-Carnitine may be employed in conjunction with CLA.

While emulsified oils according to embodiments of the present disclosure have been described as including coconut oil, coconut oil blends that are high in MCTs such as LouAna® liquid coconut oil, pure MCT oils, and Omega-3 oils, it should be appreciated that other oils having health benefits in the human diet may be emulsified using the method according to embodiments of the present disclosure and achieve similar results.

Some embodiments of the present disclosure may include a humectant which may include but is not limited to, glycerine, honey, sugar, syrup, sorbitol, aloe vera, egg yolk, and/or egg white. Inclusion of one or more of these humectants may lower water activity (aw) in the resultant emulsified oils. Water activity may be defined as the ratio between the vapor pressure of the emulsified oil itself and the vapor pressure of distilled water under identical conditions. In embodiments of the present disclosure, inclusion of humectants may reduce water activity below 0.9, and in an embodiment of the present disclosure, water activity may be reduced below 0.85. By reducing the water activity, the need for preservatives may be reduced or even eliminated, as there is less chance of microbiological growth. The humectant could be added after the emulsion has been formed to assist in thorough formation of the emulsion and consistent mixing of the humectant. In further embodiments of the present disclosure, collagen may be included in emulsified oils. The collagen may be added to the oils prior to formation of the emulsion.

Although high shear devices are commonly used for forming emulsions, a sonicator or ultra sonicator may also be used in place of a high shear mixer.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. An emulsified oil, the emulsified oil comprising:
   water;
   an oil selected from the group consisting of: coconut oil, a coconut oil blend including medium-chain triglycerides (MCTs), pure MCT oil, Omega-3 oil, cannabidiol (CBD), *Cannabis sativa* extract, tree nut oil, macadamia oil, almond oil, cashew oil, avocado oil, docosahexaenoic acid (DHA), fish oil, and/or conjugated linoleic acid (CLA);
   collagen;

a humectant that reduces water activity below 0.9; and
an emulsifier selected from the group consisting of: a pholphid, sodium stearoyl lactylate (SSL), acacia gum, beta-cyclodextrin, and combinations of same,
wherein the emulsified oil contains greater than 2% and up to 5% by volume of the emulsifier.

2. The emulsified oil of claim 1, wherein water and the oil are emulsified at a ratio of approximately 15:85 with to form an emulsified cream shot.

3. The emulsified oil of claim 1, wherein water and the oil are emulsified at a ratio of approximately 51:49 to form an emulsified cream substitute.

4. The emulsified oil of claim 1, wherein the water activity is reduced below 0.85.

5. The emulsified oil of claim 1 further comprising: one or more flavorings and/or sweeteners.

6. The emulsified oil of claim 1 further comprising: L-carnitine.

7. The emulsified oil of claim 6, wherein the emulsified oil is a cream shot comprising 1500 mg of L-Carnitine per 15 mL shot.

8. The emulsified oil of claim 1 further comprising:
at least one additional humectant selected from the group comprising: honey, sugar, syrup, sorbitol, aloe vera, egg yolk, and/or egg white.

9. An emulsified cream shot, the emulsified cream shot comprising:
water;
an oil selected from the group consisting of: coconut oil, a coconut oil blend including medium-chain triglycerides (MCTs), pure MCT oil, Omega-3 oil, cannabidiol (CBD), *Cannabis sativa* extract, tree nut oil, macadamia oil, almond oil, cashew oil, avocado oil, docosahexaenoic acid (DHA), fish oil, and/or conjugated linoleic acid (CLA);
one or more flavorings and/or sweeteners;
L-carnitine, the emulsified cream shot comprising 1500 mg of L-Carnitine per 15 mL shot; and
an emulsifier selected from the group consisting of: a pholphid, sodium stearoyl lactylate (SSL), acacia gum, beta-cyclodextrin, and combinations of same,
wherein water and the oil are emulsified at a ratio of approximately 15:85 with greater than 2% and up to 5% by volume of the emulsifier.

10. The emulsified cream shot of claim 9 further comprising: at least one humectant that reduces water activity of the emulsified cream shot below 0.9.

11. The emulsified cream shot of claim 10, wherein the at least one humectant reduces water activity of the emulsified cream shot below 0.85.

12. An emulsified cream substitute, the emulsified cream substitute comprising:
water;
an oil selected from the group consisting of: coconut oil, a coconut oil blend including medium-chain triglycerides (MCTs), pure MCT oil, Omega-3 oil, cannabidiol (CBD), *Cannabis sativa* extract, tree nut oil, macadamia oil, almond oil, cashew oil, avocado oil, docosahexaenoic acid (DHA), fish oil, and/or conjugated linoleic acid (CLA); and
an emulsifier selected from the group consisting of: a pholphid, sodium stearoyl lactylate (SSL), acacia gum, beta-cyclodextrin, and combinations of same,
wherein water and the oil are emulsified at a ratio of approximately 51:49 with greater than 2% and up to 5% by volume of the emulsifier.

13. The emulsified cream substitute of claim 12 further comprising: one or more flavorings.

14. The emulsified cream substitute of claim 12 further comprising: L-carnitine.

15. The emulsified cream substitute of claim 12 further comprising: at least one humectant that reduces water activity of the emulsified cream shot below 0.9.

16. The emulsified cream substitute of claim 15, wherein the at least one humectant reduces water activity of the emulsified cream shot below 0.85.

17. The emulsified oil of claim 1, wherein the emulsifier is amphiphilic.

* * * * *